(12) United States Patent
Fojtik

(10) Patent No.: US 8,539,644 B2
(45) Date of Patent: Sep. 24, 2013

(54) HINGE ASSEMBLY FOR AN INJECTOR

(75) Inventor: Shawn P. Fojtik, Park City, UT (US)

(73) Assignee: Mallinckrodt LLC, Hazelwood, MO (US)

( * ) Notice: Subject to any disclaimer, the term of this patent is extended or adjusted under 35 U.S.C. 154(b) by 291 days.

(21) Appl. No.: 12/738,845

(22) PCT Filed: Apr. 23, 2008

(86) PCT No.: PCT/US2008/061249
§ 371 (c)(1),
(2), (4) Date: Jun. 3, 2010

(87) PCT Pub. No.: WO2009/055087
PCT Pub. Date: Apr. 30, 2009

(65) Prior Publication Data
US 2010/0274197 A1    Oct. 28, 2010

(51) Int. Cl.
*E05F 1/02*    (2006.01)
(52) U.S. Cl.
USPC .......................................................... 16/314
(58) Field of Classification Search
USPC ........... 16/314, 292, 297, 317, 319, 328–330; 604/187
See application file for complete search history.

(56) References Cited

U.S. PATENT DOCUMENTS

| | | | |
|---|---|---|---|
| 530,187 A | 12/1894 | Lasky | |
| 870,573 A | 11/1907 | Myers | |
| 901,567 A | 10/1908 | Utschig | |
| 1,019,207 A | 3/1912 | Ward | |
| 1,218,513 A | 3/1917 | Biron | |
| 1,718,596 A | 8/1927 | Smith | |
| 3,016,897 A | 1/1962 | Kendrick | |
| 3,110,310 A * | 11/1963 | Cislak | ............................ 604/209 |
| 3,598,293 A | 8/1971 | Lee | |
| 3,770,169 A | 11/1973 | Roach | |
| 4,020,838 A | 5/1977 | Phillips et al. | |
| 4,204,539 A | 5/1980 | Van Brugge | |

(Continued)

FOREIGN PATENT DOCUMENTS

DE    196 47 529    5/1998
DE    197 32 332    2/1999

(Continued)

OTHER PUBLICATIONS

Gardiner et al., "Selective Coronary Angiography Using a Power Injector", Am. J. Roentgenole, Apr. 1986, pp. 831-833.

(Continued)

*Primary Examiner* — Victor Batson
*Assistant Examiner* — Matthew Sullivan

(57) ABSTRACT

A locking hinge assembly for an injector is disclosed. The injector includes a forward handle member, a rear handle member and a hinge connecting the first and second members and defining an axis of rotation. The locking hinge assembly includes a hinge element slidable along the axis of rotation between a locked position and an unlocked position. The hinge element is coupled to the forward handle member and the rear handle member at the hinge, and the hinge element includes at least one groove. Additionally, a locking element is provided and positioned about the hinge. The locking element is configured to be received in the groove such that rotation of the forward handle member and rear handle member about the axis of rotation is prevented when the hinge element is in the locked configuration.

12 Claims, 6 Drawing Sheets

(56) References Cited

U.S. PATENT DOCUMENTS

| | | | |
|---|---|---|---|
| 4,330,070 A | 5/1982 | Doubleday | |
| 4,364,388 A | 12/1982 | Cech | |
| 4,425,121 A | 1/1984 | Young et al. | |
| 4,712,545 A | 12/1987 | Honkanen | |
| 4,738,664 A * | 4/1988 | Prindle | 604/228 |
| 4,744,789 A | 5/1988 | Johnson | |
| 4,808,165 A | 2/1989 | Carr | |
| 4,832,692 A | 5/1989 | Box et al. | |
| 4,861,339 A | 8/1989 | Jonischkeit | |
| 4,923,096 A | 5/1990 | Ennis, III | |
| 4,968,303 A | 11/1990 | Clark et al. | |
| 4,994,065 A | 2/1991 | Gibbs et al. | |
| 5,027,605 A | 7/1991 | Hardesty | |
| 5,037,399 A | 8/1991 | Reichert et al. | |
| 5,069,421 A | 12/1991 | Kishi et al. | |
| 5,078,690 A | 1/1992 | Ryan | |
| 5,112,307 A | 5/1992 | Haber et al. | |
| 5,123,768 A * | 6/1992 | Franklin | 403/96 |
| 5,133,483 A | 7/1992 | Buckles | |
| 5,135,507 A | 8/1992 | Haber et al. | |
| 5,139,488 A | 8/1992 | Klein | |
| 5,150,488 A | 9/1992 | Yuan et al. | |
| 5,176,647 A | 1/1993 | Knoepfler | |
| 5,188,610 A | 2/1993 | Rains | |
| 5,228,883 A | 7/1993 | Blakely et al. | |
| 5,288,285 A | 2/1994 | Carter | |
| 5,304,147 A | 4/1994 | Johnson et al. | |
| 5,306,147 A | 4/1994 | Dragan et al. | |
| 5,306,248 A | 4/1994 | Barrington | |
| 5,308,358 A | 5/1994 | Bond et al. | |
| 5,336,201 A | 8/1994 | Von der Decken | |
| 5,336,238 A * | 8/1994 | Holmes et al. | 606/208 |
| 5,350,365 A | 9/1994 | De Godoy Moreira | |
| 5,368,202 A | 11/1994 | Smrt | |
| 5,425,743 A | 6/1995 | Nicholas | |
| 5,480,409 A | 1/1996 | Riza | |
| 5,499,998 A | 3/1996 | Meade | |
| 5,507,727 A | 4/1996 | Crainich | |
| 5,507,730 A | 4/1996 | Haber et al. | |
| 5,511,556 A | 4/1996 | DeSantis | |
| 5,531,708 A | 7/1996 | Woodruff | |
| 5,560,373 A | 10/1996 | De Santis | |
| 5,562,655 A | 10/1996 | Mittelstadt et al. | |
| 5,591,135 A | 1/1997 | Sullivan | |
| 5,591,176 A | 1/1997 | Henderson et al. | |
| 5,645,561 A | 7/1997 | Smith et al. | |
| 5,722,829 A | 3/1998 | Wilcox et al. | |
| 5,733,258 A | 3/1998 | Lane | |
| 5,735,874 A | 4/1998 | Measamer et al. | |
| 5,749,968 A | 5/1998 | Melanson et al. | |
| 5,755,362 A | 5/1998 | Rodriguez, Jr. et al. | |
| 5,807,340 A | 9/1998 | Pokras | |
| 5,830,194 A | 11/1998 | Anwar et al. | |
| 5,851,214 A * | 12/1998 | Larsen et al. | 606/170 |
| 5,867,911 A * | 2/1999 | Yates et al. | 30/276 |
| 5,881,928 A | 3/1999 | Register et al. | |
| 5,893,488 A | 4/1999 | Hoag et al. | |
| 5,951,517 A | 9/1999 | Lampropoulos et al. | |
| 5,961,494 A | 10/1999 | Hogan | |
| 5,961,496 A | 10/1999 | Nielsen et al. | |
| 5,964,380 A | 10/1999 | Hazzard et al. | |
| 5,964,736 A | 10/1999 | Lane | |
| 5,992,694 A | 11/1999 | Keller | |
| 6,007,515 A | 12/1999 | Epstein et al. | |
| 6,024,728 A | 2/2000 | Schulz | |
| 6,030,368 A | 2/2000 | Anwar et al. | |
| 6,047,861 A | 4/2000 | Vidal et al. | |
| 6,080,136 A | 6/2000 | Trull et al. | |
| 6,095,814 A | 8/2000 | Petrich et al. | |
| 6,117,158 A | 9/2000 | Measamer et al. | |
| 6,161,982 A * | 12/2000 | Cole | 403/97 |
| 6,183,444 B1 | 2/2001 | Glines et al. | |
| 6,213,984 B1 | 4/2001 | Lane et al. | |
| 6,241,708 B1 | 6/2001 | Reilly et al. | |
| 6,264,637 B1 | 7/2001 | Hogan | |
| 6,368,307 B1 | 4/2002 | Ziemba et al. | |
| 6,406,460 B1 | 6/2002 | Hogan | |
| 6,439,439 B1 | 8/2002 | Rickard et al. | |
| 6,585,696 B2 | 7/2003 | Peterson et al. | |
| 6,607,512 B2 | 8/2003 | Oliver et al. | |
| 6,752,781 B2 | 6/2004 | Landau et al. | |
| 6,764,466 B1 | 7/2004 | Staats et al. | |
| 6,802,824 B2 | 10/2004 | Mickley et al. | |
| 7,041,084 B2 | 5/2006 | Fotjik | |
| 7,097,636 B2 | 8/2006 | Pessin | |
| 7,125,395 B2 | 10/2006 | Hommann et al. | |
| 7,591,604 B2 * | 9/2009 | Roberts | 403/101 |
| 7,617,569 B2 * | 11/2009 | Liao | 16/334 |
| 2002/0022805 A1 | 2/2002 | Lane | |
| 2002/0183698 A1 | 12/2002 | Quinn et al. | |
| 2003/0060777 A1 | 3/2003 | Benz et al. | |
| 2004/0116873 A1 | 6/2004 | Fojtik | |
| 2004/0116893 A1 | 6/2004 | Spohn et al. | |
| 2004/0164097 A1 | 8/2004 | Orecchia et al. | |
| 2004/0210200 A1 | 10/2004 | Gerondale et al. | |
| 2004/0247453 A1 | 12/2004 | Denolly | |
| 2005/0070848 A1 | 3/2005 | Kim et al. | |
| 2005/0070912 A1 | 3/2005 | Voellmicke | |
| 2005/0137575 A1 | 6/2005 | Thompson et al. | |
| 2006/0247578 A1 | 11/2006 | Arguedas et al. | |
| 2006/0270996 A1 | 11/2006 | Fojtik | |
| 2007/0010788 A1 | 1/2007 | Evans | |
| 2007/0265573 A1 | 11/2007 | Fojtik | |
| 2010/0268116 A1 * | 10/2010 | Fojtik | 600/566 |

FOREIGN PATENT DOCUMENTS

| | | |
|---|---|---|
| EP | 0 474 218 | 3/1992 |
| EP | 0 565 045 | 10/1993 |
| EP | 0 919 251 | 6/1999 |
| EP | 1 066 797 | 1/2001 |
| EP | 1 148 834 | 10/2001 |
| EP | 1 301 227 | 4/2003 |
| EP | 1 440 706 | 7/2004 |
| FR | 2 009 514 | 2/1970 |
| FR | 2 683 140 | 5/1993 |
| FR | 2 848 860 | 6/1994 |
| JP | 59 48641 | 3/1984 |
| JP | 1 138370 | 9/1989 |
| JP | 6 296618 | 10/1994 |
| WO | WO 99/08735 | 2/1999 |
| WO | WO 2004/062713 | 7/2004 |

OTHER PUBLICATIONS

Ganeshkumar et al., "Traditional Versus Automated Injection Contrast System in Diagnostic . . . ", J. Invasive Cardiol., 16(7), 2004, pp. 360-362.

Call et al., "Automated contrast Injection in Contemporary Practice During Cardiac . . . ", J. Invasive Cardiol., 18(10), 2006, pp. 469-471.

Saito et al., "Evaluation of New 4 French Catherters by Comparison to 6 French Coronary Artery Images", J. Invasive Cardiol., 11(1), 1999, pp. 13-30.

* cited by examiner

HINGE ASSEMBLY FOR AN INJECTOR

CROSS REFERENCE TO RELATED APPLICATIONS

This application is a national stage application of PCT/US2008/061249, filed Apr. 23, 2008, which claims the benefit of U.S. patent application Ser. No. 11/923,514, filed Oct. 24, 2007.

BACKGROUND

The field of the invention relates generally to hand-held injectors and syringes, and more specifically to locking hinge assemblies for such injectors and syringes.

SUMMARY

One aspect is directed to a locking hinge assembly for an injector. The injector includes a forward handle member, a rear handle member and a hinge connecting the first and second members and defining an axis of rotation. The locking hinge assembly includes a hinge element slidable along the axis of rotation between a locked position and an unlocked position. The hinge element is coupled to the forward handle member and the rear handle member at the hinge, and the hinge element includes at least one groove. Additionally, a locking element is positioned about the hinge. The locking element is configured to be received in the groove such that rotation of the forward handle member and rear handle member about the axis of rotation is prevented when the hinge element is in the locked configuration.

Another aspect is directed to an injector including a syringe barrel having a receptacle configured to receive a fluid. A plunger is configured to slidably translate through the receptacle. The injector also includes a forward handle member, a rear handle member, and a locking hinge assembly. The forward handle member includes an internal housing having a non-circular aperture therethrough, a proximal end configured to be pivotally coupled to the plunger, and a distal end positioned opposite the proximal end. The rear handle member includes a proximal end having two arms separated by a distance, wherein each of the arms is configured to be pivotally coupled to the syringe barrel and to rotatably engage the forward member at a hinge. The rear handle member also includes a distal end configured to translate the plunger through the receptacle when used with the forward member distal end. The locking hinge assembly is positioned within the housing and extends outward through the non-circular aperture. The locking hinge assembly includes a hinge element slidable along the axis of rotation between a locked position and an unlocked position, wherein the hinge element includes a first end having a non-circular cross-section, a second end having a non-circular cross-section, and at least one groove. The locking hinge assembly also includes a locking element positioned within the housing and is configured to be received in the groove such that rotation of the forward handle member and rear handle member about the axis of rotation is prevented when the hinge element is in the locked position.

Still another aspect is directed to a locking hinge assembly for an injector that includes a forward handle member, a rear handle member and a hinge connecting the first and second members and defining an axis of rotation. The hinge assembly is slidable along the axis of rotation between a locked position and an unlocked position, and includes a first hinge member having a first portion, an intermediate portion, and a second portion. The first portion includes a non-circular cross-section. The intermediate portion includes a flange including at least one groove, and the second portion includes an extension. The hinge assembly also includes a second hinge member having a first portion and an opposite second portion. The first portion includes a cavity configured to receive the first hinge member extension, and the second portion includes a non-circular cross-section. A biasing member is positioned within the second hinge member cavity and is configured to exert an force outward against first and second hinge members. A locking element is positioned about the hinge and is configured to be received in the groove such that rotation of the forward handle member and rear handle member about the axis of rotation is prevented when the hinge element is in the locked position.

Various refinements exist of the features noted in relation to the above-mentioned aspects of the present invention. Further features may also be incorporated in the above-mentioned aspects of the present invention as well. These refinements and additional features may exist individually or in any combination. For instance, various features discussed below in relation to any of the illustrated embodiments of the present invention may be incorporated into any of the above-described aspects of the present invention, alone or in any combination.

DETAILED DESCRIPTION

Figure 1:
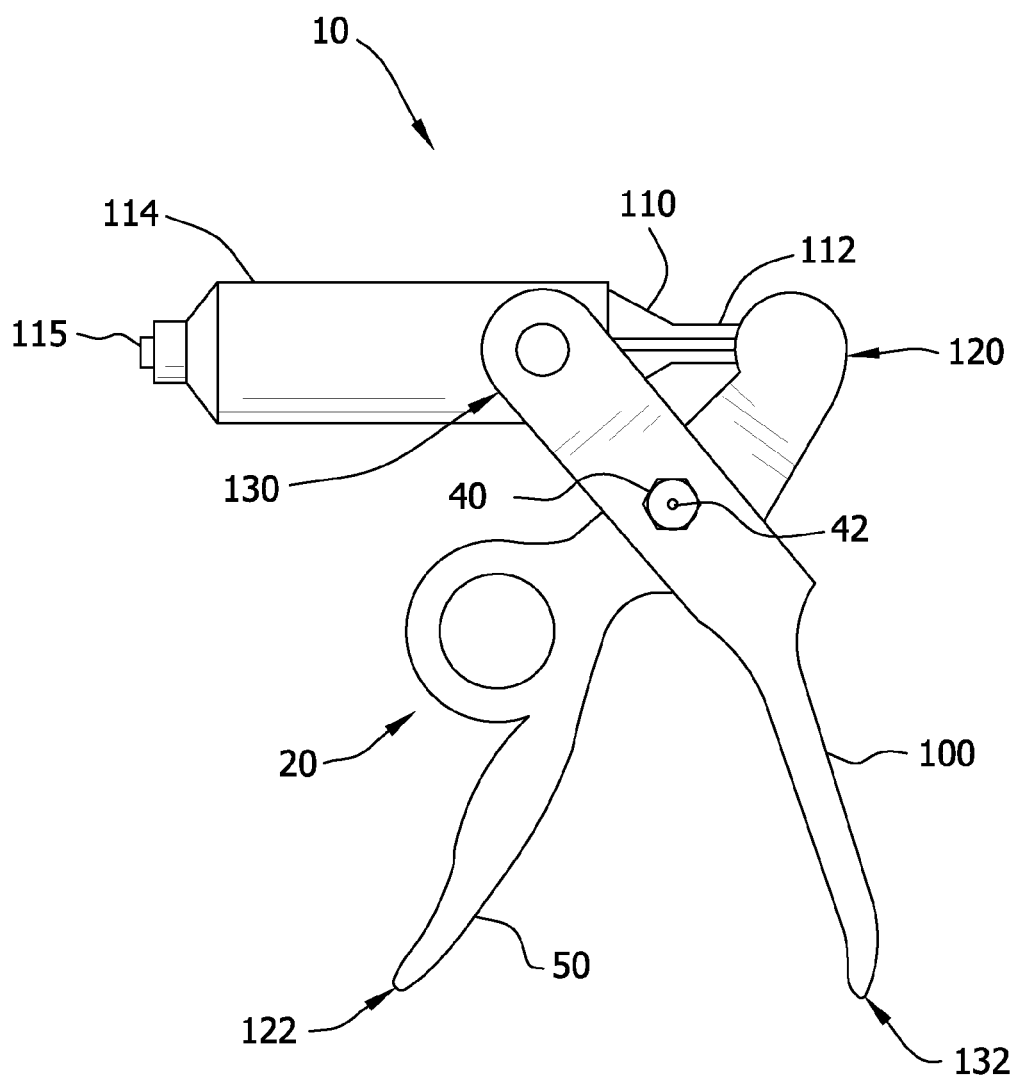
FIG. 1 is a left side view of an exemplary injector.

FIG. 1 is a side view of an exemplary embodiment of an injector 10. In the exemplary embodiment, injector 10 includes a handle assembly 20 having a forward handle member 50 and a rear handle member 100. Injector 10 includes a plunger 110 partially received in barrel 114. The plunger 110 has an end 112 that is not received in barrel 114. Barrel 114 is adapted to receive a quantity of fluid (not shown). The fluid can be selectively forced out of the barrel through nozzle 115. The fluid in the barrel is not limited to the following, but may be for example, a medication, a contrast agent, or a gas for inflation of a balloon or catheter.

Forward handle member 50 includes a proximal end 120 configured to be coupled to plunger first end 112, and a distal end 122 opposite the proximal end 120. Similarly, rear handle member 100 includes a proximal end 130 that is configured to be coupled to the syringe barrel 114, and a distal end 132 opposite the proximal end 130. Additionally, handle assembly 20 includes a hinge 40 that pivotally connects forward handle member 50 and rear handle member 100 to one another. In the exemplary embodiment, hinge 40 also includes a locking hinge assembly 42 that is configured to enable forward handle member 50 and rear handle member 100 to be locked into a plurality of different positions, including an open position, in which handle member distal ends 122, 132 are rotated as far as possible apart from one another (as shown in FIG. 1, for example), and a closed position, in which handle member distal ends 122, 132 are rotated as close as possible to one another (not shown). By locking the relative positions of members 50 and 100, locking hinge assembly 42 may prevent or limit further movement of members 50 and 100. Though the hinge 40 is shown herein as a multi-piece assembly, it may also be a single, unitary piece.

Figure 2:
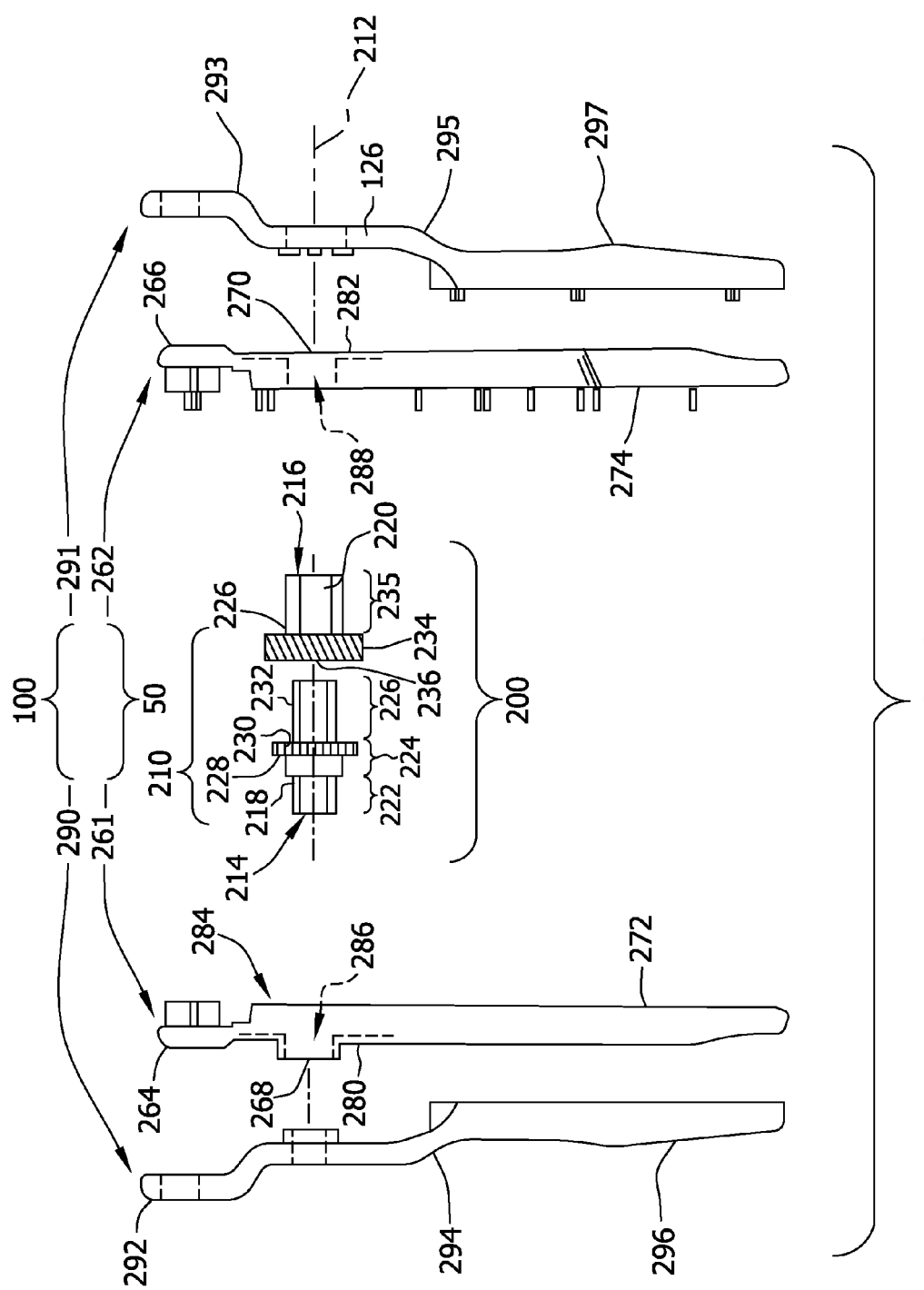
FIG. 2 is an exploded rear view of an exemplary locking hinge assembly in the injector of FIG. 1.
Figure 3:
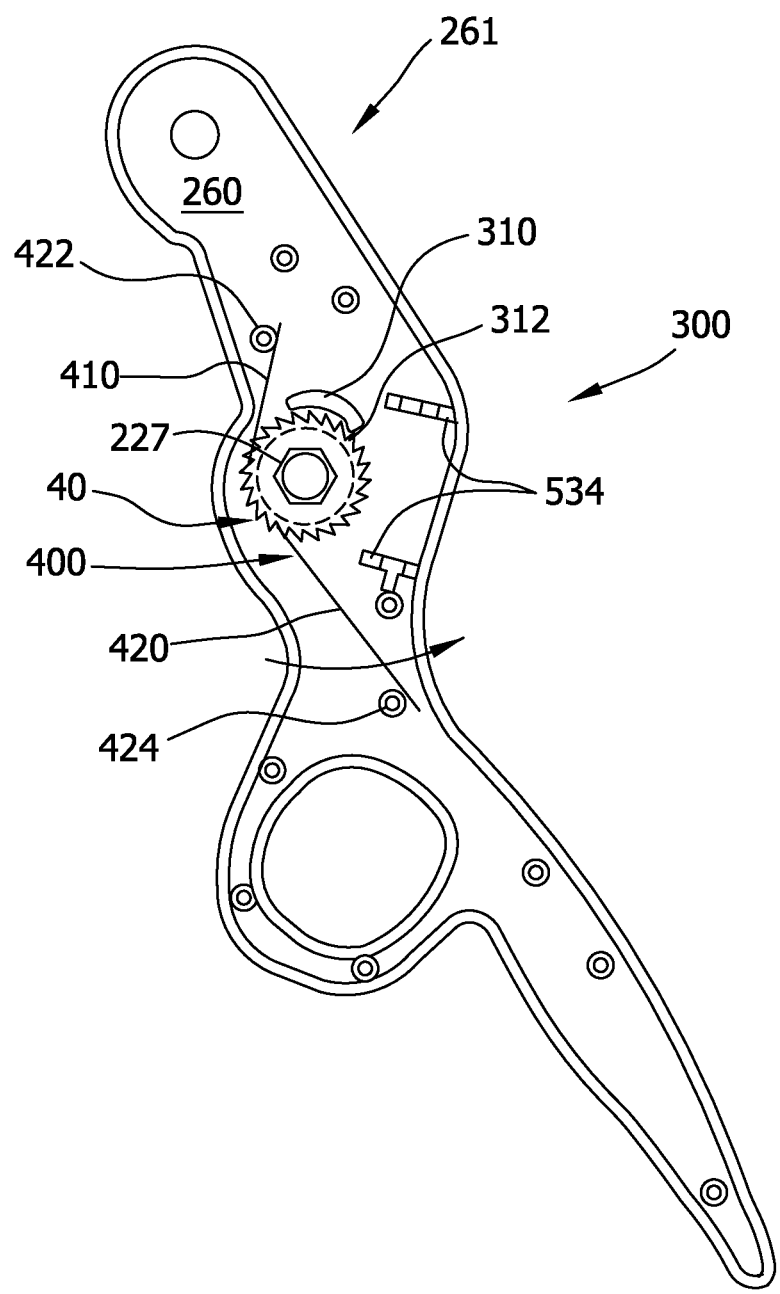
FIG. 3 is a left side view of portions of the exemplary locking hinge assembly of FIG. 2.

Referring to FIGS. 2 and 3, FIG. 2 is an exploded view of an exemplary locking hinge assembly 200 used with the injector 10 shown in FIG. 1. FIG. 3 is a side view of the exemplary locking hinge assembly 200 used with injector 10. Hinge 40 includes an elongate hinge element 210 with a central axis 212, or axis of rotation, about which hinge 40 is intended to rotate, and two ends 214, 216. At least one end 214, 216 of elongate hinge element 210 is configured to engage a complementary portion of member 50, 100 (shown in FIG. 1).

In the exemplary embodiment, elongate hinge element 210 includes a first hinge member 218 and a second hinge member 220 that are each configured for assembly with one another. First hinge member 218 includes a first portion 222, an intermediate portion 224, and a second portion 226, wherein the first portion 222 comprises a non-circular cross-section 227 (shown in FIG. 3), and wherein the intermediate portion comprises a flange 228 having at least one groove 230. More specifically and in the exemplary embodiment, flange 228 includes a plurality of tooth and groove elements. Alternatively, flange 228 includes any configuration that enables hinge 40 and hinge element 210 to function as described herein. The second portion 226 includes an extension 232. Second hinge member 220 includes a first portion 234 and an opposite second portion 235. First portion 234 includes a cavity 236 configured to receive the first hinge member extension 232, and wherein the second portion 235 includes a non-circular cross-section. Alternatively, a single piece hinge may be used (not shown).

In operation, forward handle member 50 is configured to be held and operated by a user's hand (not shown), specifically and in the exemplary embodiment, by the user's fingers. Second member 100 is configured to he held by a palm and thumb of a user's hand, and is pivotally coupled to a barrel 114 (shown in FIG. 1). When proximal ends 120, 130 of members 50 and 100, respectively, are drawn toward one another, members 50 and 100 pivot about central axis 212 of hinge 40, forcing distal ends 122, 132 toward one another, and moving plunger 110 distally into barrel 114. Due to its location and configuration, hinge 40 may be slid between unlocked, intermediate, and locked positions with a finger of thumb of a user's hand. More specifically, a finger or thumb on the same hand that holds handle 20 may be used to move hinge 40 to the desired position.

In the exemplary embodiment, forward handle member 50 includes an inner surface 260 and two elements 261, 262, each forming a side half of member 50 and configured to be assembled with each other. Each element 261, 262 includes a proximal portion 264, 266, an intermediate portion 268, 270 adjacent to proximal portions 264, 266, and a distal portion 272, 274 adjacent to intermediate portion 268, 270. Proximal portions 264, 266 and distal portions 272, 274 may be located on substantially opposite sides of intermediate portions 268, 270, respectively.

Proximal portions 264, 266 are configured to be pivotally coupled to syringe plunger 110 (shown in FIG. 1). In the exemplary embodiment, hinge members 218, 220, which are configured to align and to be assembled with each other, extend from inner surface 260. When elements 261, 262 are assembled, intermediate portions 268, 270 include spaced apart outer walls 280, 282 that define a hollow internal housing 284 that is configured to receive a central portion of hinge 40, including a hinge element 210. Intermediate portions 268, 270 include an aperture 286, 288 through each outer wall 280, 282. Apertures 286, 288 are axially aligned with each other, and are configured to receive opposite sides of hinge element 210 while permitting handle 50 to pivot freely about central axis 212 regardless of whether hinge element 210 is engaged in a locked position, as described herein.

Rear handle member 100 includes two elements 290, 291 each forming a side half of member 100 and configured to be assembled with each other. Each element 290, 291 includes a proximal portion 292, 293 an intermediate portion 294, 295 adjacent to proximal portions 292, 293 and a distal portion 296, 297 adjacent to intermediate portion 294, 295. Rear handle member 100 is fabricated such that proximal ends 292, 293 are separated by a distance L (shown in FIGS. 4 and 5), and such that the two elements 290, 291 are joined from the respective intermediate portions 294, 295 to the distal portions 292, 293. Each of the proximal portions 292, 293 are configured to pivotally couple to the syringe barrel 114 (shown in FIG. 1) and each of the proximal portions 292, 293 are configured to rotatably engage the forward member 50 at hinge 40.

Referring to FIG. 3, in the exemplary embodiment, forward handle member element inner surface 260 includes a locking feature 300 that engages hinge element 210 upon movement of hinge 40 from an intermediate position or unlocked position to a locked position. Locking feature 300 engages hinge element 210 as hinge 40 is slid along central axis 212 (shown in FIG. 2).

In the exemplary embodiment, locking element 300 includes a stationary ratchet arm 310 including a tip 312 that engages hinge element 210 within a groove 230 thereof (shown in FIG. 3). The configurations (or orientations) of grooves 230 and tip 312 enables hinge 40 to rotate in one direction (e.g., clockwise, as handles 50 and 100 are drawn together), but prevent the rotation of hinge 40 in the opposite direction (e.g., counterclockwise). Locking element 300 comprises a fixed or actuatable (e.g., with a button, slider, switch, etc.) element that limits rotation of hinge 40 in one or both directions.

As shown in FIG. 3, a biasing member (e.g. a spring) 400 is fixedly secured to hinge 40. In the exemplary embodiment, spring upper arm 410 and spring lower arm 420 are held substantially in place by two respective posts 422, 424 protruding from an inner surface 260. When proximal end 130 of member 100 pivots toward proximal end 120 of member 50 (as shown in FIG. 1), hinge 40 rotates, which introduces tension into spring lower arm 420. Once members 50 and 100 are no longer held in a closed or partially closed position of handle 20, the resiliency of biasing member 400 rotates hinge 40, causing proximal end 130 of member 100 to move away from proximal end 120 of member 50, thereby returning handle 20 to an open position.

Figure 4:
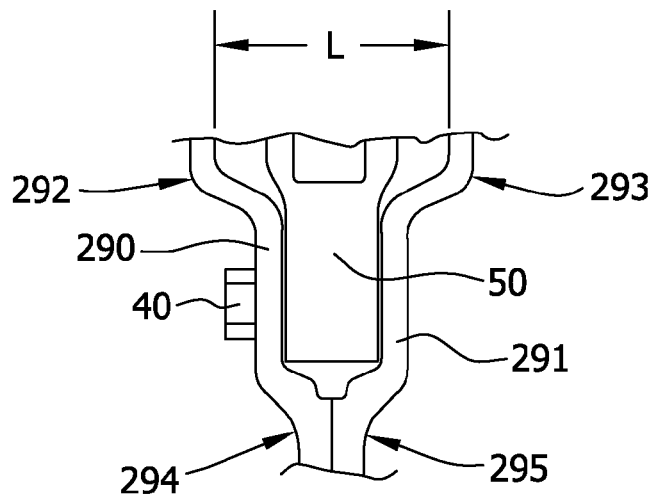
FIG. 4 is a fragmentary end view of a hinge element shown in FIG. 2 in the locked position.
Figure 5:
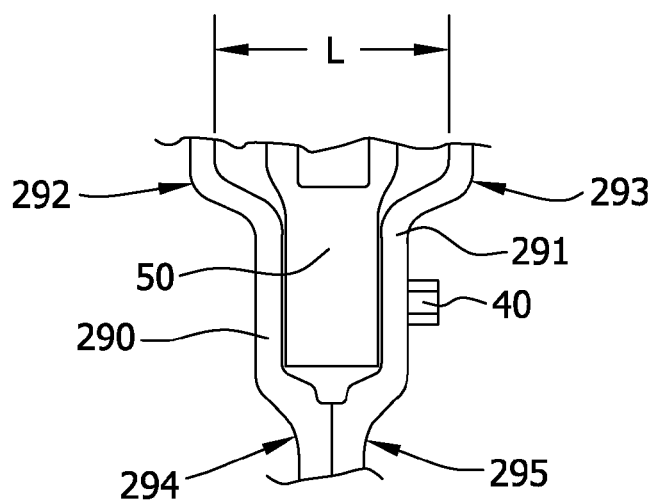
FIG. 5 is a fragmentary end view like FIG. 4 but with the hinge element in the unlocked position.
Figure 6:
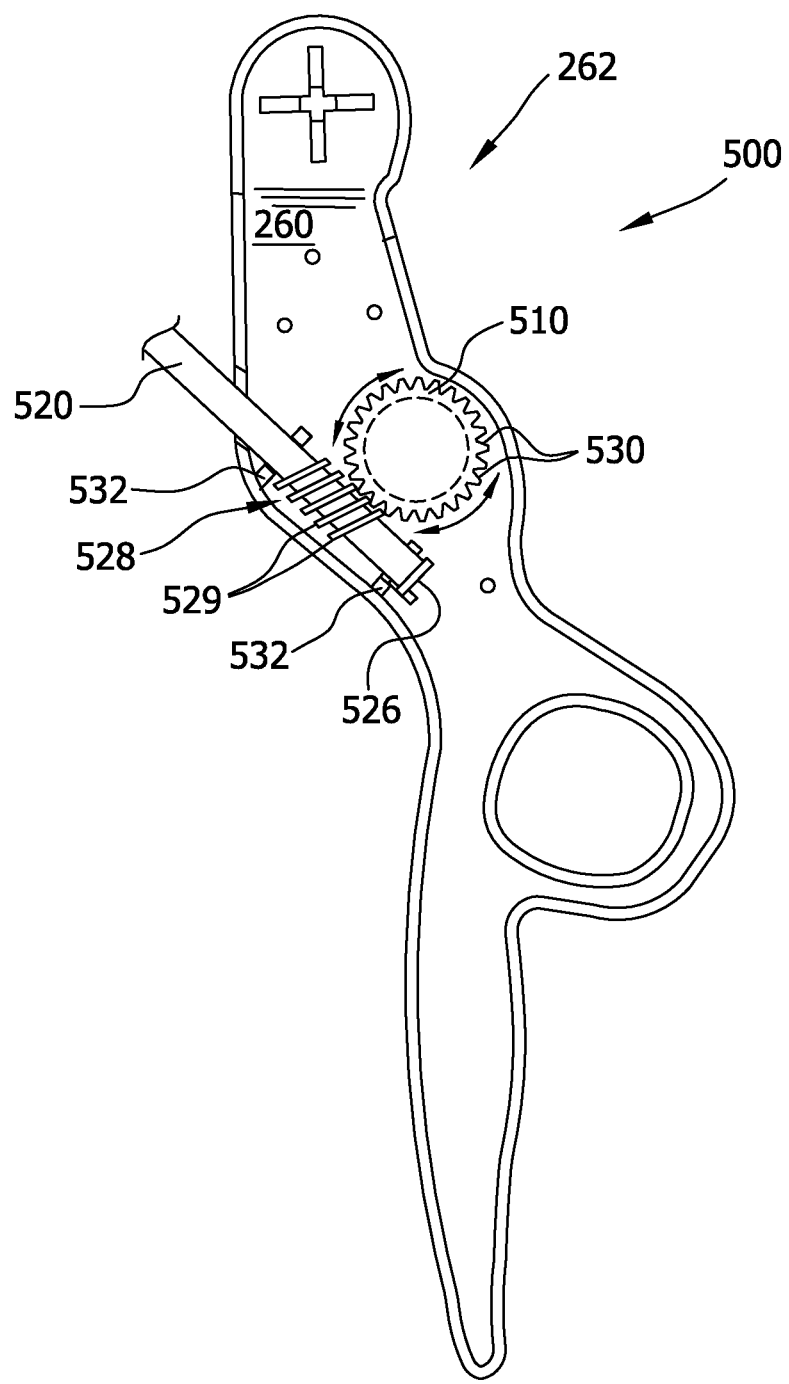
FIG. 6 is a side view of an exemplary micro-adjustment assembly used with the injector shown in FIG. 1.

FIG. 4 is a fragmentary end view of hinge element shown in FIG. 2, in the locked position. FIG. 5 is a fragmentary end view of hinge element shown in FIG. 2, in the unlocked position. In operation, member 50 (shown in FIGS. 1 and 2) pivots relative to hinge 40 regardless of whether hinge 40 is in a locked position or an unlocked position. When in the locked position (as shown in FIG. 4), hinge 40 limits or prevents member 100 from pivoting.

Figure 7:
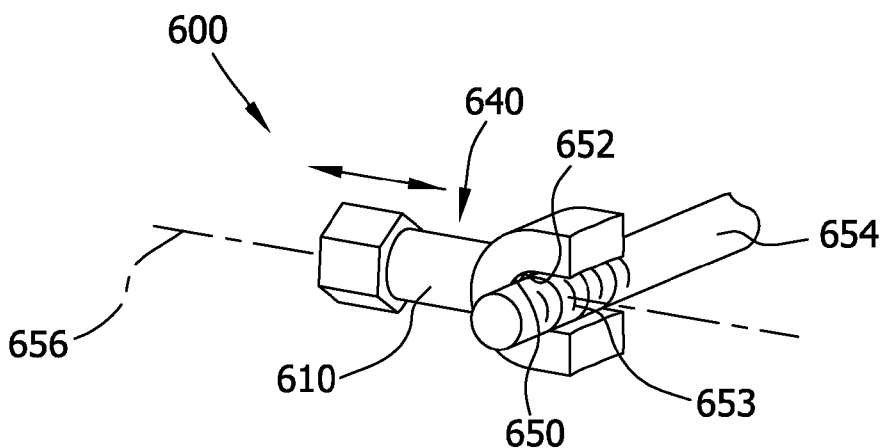
FIG. 7 is a fragmentary perspective view of an alternative micro-adjustment assembly used with the injector shown in FIG. 1.
Figure 8:
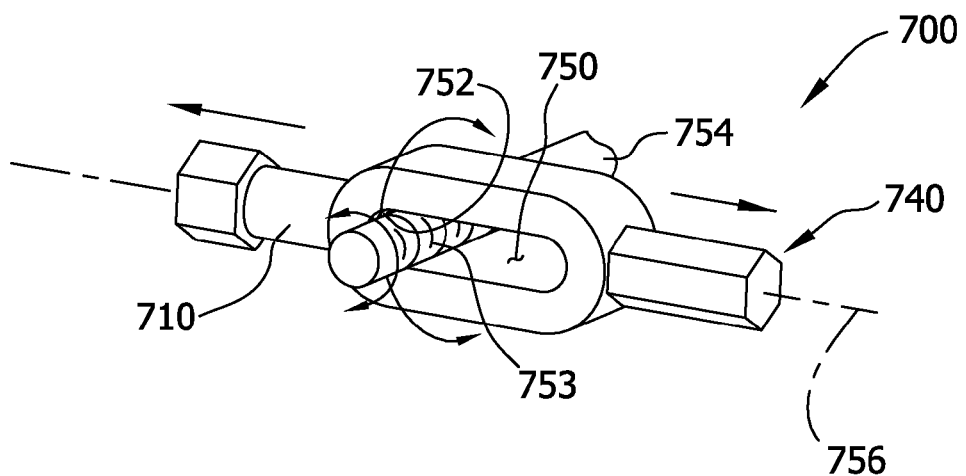
FIG. 8 is a fragmentary perspective view of another alternative micro-adjustment assembly used with the injector shown in FIG. 1.
Figure 9:
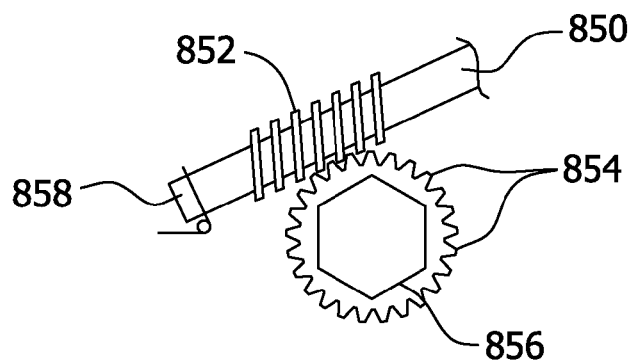
FIG. 9 is a side view of still another alternative micro-adjustment assembly used with the injector shown in FIG. 1.

Referring to FIGS. 6-9, FIG. 6 is a side view of an exemplary microadjustment assembly used with the injector shown in FIG. 1. FIG. 7 is a fragmentary elevation view of the microadjustment assembly shown in FIG. 6. FIG. 8 is a fragmentary elevation view of the microadjustment assembly shown in FIG. 6. FIG. 9 is an alternative microadjustment assembly used with the injector shown in FIG. 1. In the exemplary embodiment, hinge 40 includes a microadjustment assembly 500. Microadjustment assembly 500 includes a gear or threaded element 510 that is configured to engage a separate microadjustment screw 520. Alternatively, microadjustment element includes any type of gear that enables injector to function as described herein. In yet another embodiment, hinge 40 does not include a microadjustment assembly.

An end 526 of a microadjustment screw 520 is disposed within internal housing 528. More specifically, microadjustment screw 520 includes features 529 that are configured to engage microadjustment assembly 500. In the exemplary embodiment, features 529 include a thread of a worm gear that engages a plurality of teeth 530 of microadjustment assembly 500. Microadjustment screw 520 is secured therein by cooperating mounts 532, 534 (shown in FIG. 3) that extend within internal housing 528. As microadjustment screw 520 is rotated, microadjustment assembly 500 and hinge 40 also rotate.

The relative positions of members 50 and 100 of handle 20 may be locked into place by engaging microadjustment assembly 500 with microadjustment screw 520. When hinge 40 is slid into an intermediate position (i.e., a position between the locked position shown in FIG. 4 and the unlocked position shown in FIG. 5) locking element 250 is disengaged and microadjustment screw 520 engages microadjustment assembly 500. Forward handle member 50 is held in place by microadjustment screw 520, which prevents external pivotal movement of members 50 and 100 (e.g., by squeezing members 50 and 100 together or moving them apart with a hand). Internal rotation of microadjustment assembly 500 by rotating microadjustment screw 520 will rotate elongate hinge element 210, causing rear handle member 100 to pivot relative to forward handle member 50.

Alternatively, as shown in FIG. 7, a hinge 640 includes a microadjustment element 600 at an end of elongate hinge element 610. Microadjustment element 600 includes a recess 650 in combination with engagement features 652 that are each configured to receive and engage complementary engagement features 653 of a microadjustment screw 654. Hinge 640 or microadjustment screw 654 is actuated to cause at least one of the microadjustment element 600 and microadjustment screw 654 to engage the other along a central axis 656. In this embodiment, engagement features 652 include threads complementary to threads on microadjustment screw 654 and are oriented to engage complementary splines protruding from the outer surface of microadjustment screw 654, or any other suitable engagement features that cooperate with corresponding engagement features on microadjustment screw 654.

In yet another embodiment, as shown in FIG. 8, a hinge 740 includes a microadjustment element 700 at an end of elongate hinge element 710. Microadjustment element 700 includes an enclosed channel 750 in combination with engagement features 752 that are each configured to receive and engage complementary engagement features 753 of a microadjustment screw 754. Hinge 740 or microadjustment screw 754 is actuated to cause at least one of the microadjustment element 700 and microadjustment screw 754 to engage the other along a central axis 756. In this embodiment, engagement features 752 include threads complementary to threads on microadjustment screw 754 and are oriented to engage complementary splines protruding from the outer surface of microadjustment screw 754, or any other suitable engagement features that cooperate with corresponding engagement features on microadjustment screw 754.

Alternatively, as shown in FIG. 9, a microadjustment screw 850 includes engagement features 852 that are complementary to engagement features 854 (e.g. teeth, etc.) that are moved into and out of engagement with locking element 856. An end 858 of microadjustment screw 850 may be associated with a handle 20 (see, e.g., FIG. 1) in such a way that microadjustment screw 850 pivots from the end thereof while remaining free to rotate. Accordingly, a knob (not shown) at the opposite end of microadjustment screw 850 may be moved to tilt engagement features 854 of microadjustment screw 850 into and out of engagement with engagement features 854.

Exemplary embodiments of locking hinge assemblies are described in detail above. The above-described assemblies for locking the handles of a manually operated injector (e.g. a syringe, an aspiration device), including microadjustment assemblies may be implemented to facilitate a more accurate discharge of medium from the injector. Additionally, the systems described herein facilitate introducing accurate, small amounts of the medium to a patient, for example, in a controlled manner.

Although the apparatus and methods described herein are described in the context of using a locking hinge within an injector for use in medical devices, it is understood that the apparatus and methods are not limited to medical syringe-type injectors. Likewise, the system components illustrated are not limited to the specific embodiments described herein, but rather, system components can be utilized independently and separately from other components described herein.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

While the invention has been described in terms of various specific embodiments, those skilled in the art will recognize that the invention can be practiced with modification within the spirit and scope of the claims.

What is claimed is:

1. A locking hinge assembly in an injector, the injector comprising a forward handle member, a rear handle member and a hinge connecting the members and defining an axis of rotation, the locking hinge assembly comprising:

a hinge element selectively movable between a locked position and an unlocked position, the hinge element movable parallel to the axis of rotation, the hinge element coupled to the forward handle member and the rear handle member at the hinge, the hinge element comprising at least one groove; and a locking element positioned about the hinge and comprising a ratchet arm, the locking element configured to be received in the at least one groove such that rotation of the forward handle member and rear handle member about the axis of rotation is prevented when the hinge element is in the locked configuration.

2. The assembly in accordance with claim 1, wherein the hinge element further comprises a first end and a second end, each end comprising a non-circular shape.

3. The assembly in accordance with claim 2, wherein the forward handle member comprises:
   an internal housing extending around the hinge; and
   a non-circular aperture therethrough, the aperture configured to receive the hinge element first and second ends.

4. The assembly in accordance with claim 1, further comprising a micro-adjust assembly comprising:
   a microadjustment screw comprising a exposed portion and an enclosed portion;
   a flange positioned circumferentially around the hinge element; and
   a groove within the flange and configured to receive the microadjustment screw.

5. The assembly in accordance with claim 4, wherein the groove is disposed between a plurality of teeth on the flange.

6. The assembly in accordance with claim 5, wherein the microadjustment screw further comprises a worm gear configured to rotate the hinge element via the plurality of teeth.

7. The assembly in accordance with claim 1, wherein the at least one groove is disposed between a plurality of teeth on the flange.

8. A locking hinge assembly in an injector, the injector comprising a forward handle member and a rear handle member connected at a hinge defining an axis of rotation, the hinge assembly slidable along the axis of rotation between a locked position and an unlocked position, the locking hinge assembly comprising:
   a first hinge member comprising a first portion, an intermediate portion, and a second portion, wherein the first portion comprises a non-circular cross-section, wherein the intermediate portion comprises a flange comprising at least one groove, and wherein the second portion comprises an extension;
   a second hinge member comprising a first portion and an opposite second portion, wherein the first portion comprises a cavity configured to receive the first hinge member extension, and wherein the second portion comprises a non-circular cross-section;
   a biasing member positioned within the second hinge member cavity and configured to exert an force outward against first and second hinge members; and
   a locking element positioned about the hinge and comprising a ratchet arm, the locking element configured to be received in the at least one groove such that rotation of the forward handle member and rear handle member about the axis of rotation is prevented when the hinge assembly is in the locked position.

9. The assembly in accordance with claim 8, wherein the at least one groove is disposed between a plurality of teeth on the flange.

10. The assembly in accordance with claim 8, further comprising a micro-adjust assembly comprising:
    a flange positioned circumferentially around the second hinge member;
    a plurality of teeth extending outwardly from the flange; and
    a microadjustment screw comprising a exposed portion and an enclosed portion, the microadjustment screw configured to engage the plurality of teeth.

11. The assembly in accordance with claim 10, wherein the microadjustment screw further comprises a worm gear configured to rotate the locking hinge assembly via the plurality of teeth.

12. The assembly in accordance with claim 8, wherein the biasing member is a spring.

* * * * *